(12) United States Patent
Yeh et al.

(10) Patent No.: US 6,760,468 B1
(45) Date of Patent: Jul. 6, 2004

(54) METHOD AND SYSTEM FOR THE DETECTION OF LUNG NODULE IN RADIOLOGICAL IMAGES USING DIGITAL IMAGE PROCESSING AND ARTIFICIAL NEURAL NETWORK

(75) Inventors: Hwa-Young Michael Yeh, Potomac, MD (US); Yuan-Ming Fleming Lure, Potomac, MD (US); Jyh-Shyan Lin, North Potomac, MD (US)

(73) Assignee: Deus Technologies, LLC, Rockville, MD (US)

( * ) Notice: Subject to any disclaimer, the term of this patent is extended or adjusted under 35 U.S.C. 154(b) by 0 days.

(21) Appl. No.: 09/503,839

(22) Filed: Feb. 15, 2000

Related U.S. Application Data

(63) Continuation-in-part of application No. 08/597,736, filed on Feb. 6, 1996, now abandoned.

(51) Int. Cl.$^7$ .............................. G06K 9/46; G06K 9/62
(52) U.S. Cl. ....................... 382/132; 382/156; 382/173; 382/203; 128/922; 128/925
(58) Field of Search .................................. 382/132, 156, 382/157, 203, 173; 128/922, 925

(56) References Cited

U.S. PATENT DOCUMENTS

| | | | |
|---|---|---|---|
| 4,538,227 A | * 8/1985 | Toraichi et al. ............... | 378/62 |
| 4,646,334 A | 2/1987 | Zerhouni | |
| 4,907,156 A | 3/1990 | Doi et al. | |
| 5,289,374 A | 2/1994 | Doi et al. | |
| 5,463,548 A | 10/1995 | Asada et al. | |
| 5,797,130 A | 8/1998 | Nelson et al. | |
| 5,799,101 A | 8/1998 | Lee et al. | |
| 5,807,256 A | 9/1998 | Taguchi et al. | |
| 5,828,774 A | 10/1998 | Wang | |
| 5,881,124 A | * 3/1999 | Giger et al. ................... | 378/8 |
| 5,987,094 A | * 11/1999 | Clarke et al. ................. | 378/62 |
| 6,088,473 A | * 7/2000 | Xu et al. ...................... | 382/132 |
| 6,141,437 A | * 10/2000 | Xu et al. ...................... | 382/130 |
| 6,240,201 B1 | * 5/2001 | Xu et al. ...................... | 382/130 |

OTHER PUBLICATIONS

Chiou et al. "Neural–Knowledge Base Object Detection in Hybrid Lung Nodule Detection (HNLD) System." IEEE World Congress on Computation Intelligence, Conference on Neural Networks, vol. 7, Jul. 1994, pp. 4180–4185.*

Kawata et al. "Classification of Pulmonary Nodules in Thin–Section CT Images Based on Shape Characterization." Int. Conf. on Image Processing, vol. 3, Oct. 1997, pp. 528–530.*

(List continued on next page.)

Primary Examiner—Jon Chang
(74) Attorney, Agent, or Firm—Venable LLP; Robert Kinberg; Jeffrey W. Gluck

(57) ABSTRACT

A method and system improve the detection of abnormalities, such as lung nodules, in radiological images using digital image processing and artificial neural network techniques. The detection method and system use a nodule phantom for matching in order to enhance the efficiency in detection. The detection method and system use spherical parameters to characterize true nodules, thus enabling detection of the nodules in the mediastinum. The detection method and system use a multi-layer back-propagation neural network architecture not only for the classification of lung nodules but also for the integration of detection results from different classifiers. In addition, this method and system improve the detection efficiency by recommending the ranking of true nodules and several false positive nodules prior to the training of the neural network classifier. The method and system use image segmentation to remove regions outside the chest in order to reduce the false positives outside the chest region.

58 Claims, 11 Drawing Sheets

OTHER PUBLICATIONS

Chabat et al. "CT Lung Image Classification with Correction for Perfusion Gradient." Seventh Int. Conf. on Image Processing and Its Applications, vol. 1, Jul. 1999, pp. 402–406.*

Kawata et al. "Classification of Pulmonary Nodules in Thin–Section CT Images by Using Multi–Scale Curvature Indexes." Int. Conf. on Image Processing, vol. 2, Oct. 1999, pp. 197–201.*

Michael F. McNitt–Gray, Feature Selection in the Pattern Classification Problem of Digital Chest Radiograph Segmentation:, Sep. 3, 1995, pp. 537–547, vol. 14, Ieee Transactions on Medical Imaging.

Shih–Chung B. Lo et al., "Computer–Assisted Diagnosis of Lung Nodule Detection Using Artificial Convolution Neural Network", Radiology Department, Georgetown University Medical Center, 1993, pp. 859–869, SPIE vol. 1898, Image Processing.

Samuel G. Armato III, Computerized Detection of Abnormal Asymmetry in digital Chest Radiographs[a], Kurt Rossmann Laboratories for Radiologic Image Research, Aug. 16, 1994, pp. 1761–1768, Med. Phys. 21 (11), Nov. 1994.

Maria J. Carreira, et al., "Automatic Segmentation of Lung Fields on Chest Radiographic Images", Computers and Biomedical Research 32, (1999), pp. 283–303, Article ID cbmr. 1999.1510.

Neal F. Vittitoe[a], "Identification of Lung Regions in Chest Radiographs Using Markov Random Field Modeling", American Assoication of Physicists in Medicine, 1998, pp. 976–985.

Akira Hasegawa, et al., "A Shift–Invariant Neural Network for the Lung Field Segmentation in Chest Radiography", Journal of VLSI Signal Processing 18, pp. 241–250, 1998, Kluwer Academic Publishers, Netherlands.

Osamu Tsujii, et al., "Automated Segmentation of anatomic Regions in Chest Radiographs Using an Adaptive–Sized Hybrid Neural Network", Department of Radiology, Georgetown University Medical Center, Washington, DC, 1998, pp. 998–1007.

Jyh–Shyan Lin, "Reduction of False Positives in Lung Nodule Detection Using a Two–Level Neural Classification", IEEE Transactions on Medical Imaging, vol. 15, No. 2, 1996, pp. 206–217.

Shih–Chung B. Lo, et al., "Automatic Lung Nodule Detection Using Profile Matching and Back–Propagation Neural Network Techniques", Journal of Digital Imaging, vol. 6, No. 1, 1993, pp. 48–54.

Shih–Chung B Lo,"Artificial Convolution Neural Network Techniques and Applications for Lung Nodule Detection", The IEEE Trans. on Medical Imaging, vol. 14, No. 4, 1995, pp. 711–719.

Ewa, Pietka, "Lung Segmentation in Digital Radiographs", Journal of Digital Imaging, vol. 7, No. 2, 1994, pp. 79–84.

Yun–Shu P. Chiou[s], "Application of Neural Network Based Hybrid System for Lung Nodule Detection", Computer–Based medical Systems Symposium, CBMS 93, Ann Arbor, 1993,.

Yulei Jiang, MS, et al., "A Receiver Operating Characteristic Partial Area Index for Highly Sensitive Diagnostic Tests[1]", 1996,.

Jyh–Shyan Lin, "Differentiation Between Nodules and End–On Vessels Using A Convolution Neural Network Architecture", Journal of Digital Imaging, Vo. 8, No. 3, 1995, pp. 132–141.

Anil K. Jain, "Fundamentals of Digital Image Processing" pp. 246–253, pp. 380–387.

William K. Pratt, "Digital Image Processing", pp. 472–476, pp. 613–363.

Simon Haykin, "Neural Networks, A Comprehensive Foundation", pp. 179–181, pp. 409–412.

Chiou, Y.S.P., et al., "Neural Network Image Analysis and Classification in Hybrid Lung Nodule Detection (HLND) System", IEEE, 1993, pp. 517–526.

Maryellen Lissak Giger, "Computerized Scheme for the Detection of Pulmonary Nodules", IEEE Enginering in Medicine & Biology Society 11th Annual International Conference, 1989.

Jeff Duryea, et al. "Digitally Automated Algorithm for the Segmentation of Lung Fields on Digital Chest Radiographic Images", Med. Phys, vol. 22, No. 2, 1995, pp. 183–191.

Chiou, Y.S.P., and Lure, Y.M.F., "Hybrid Lung Nodule Detection (HLND) System," *Cancer Letters* 77, 1994, pp. 119–126.

Lo, S.–C. B., et al., "Computer–Assisted Diagnosis of Lung Nodule Detection Using Artificial Convolution Neural Network," *SPIE vol. 1898 Image Processing,* 1993, pp. 859–869.

* cited by examiner

| Eight Types of Anatomic Structures ||||||||
|---|---|---|---|---|---|---|---|
| True Nodule (TN) | Rib Crossing (RX) | Rib Vessel Crossing (RV) | Vessel Cluster (VC) | End Vessel (EV) | Rib Edge (RE) | Bone (BO) | Vessel (VS) |

FIGURE 7

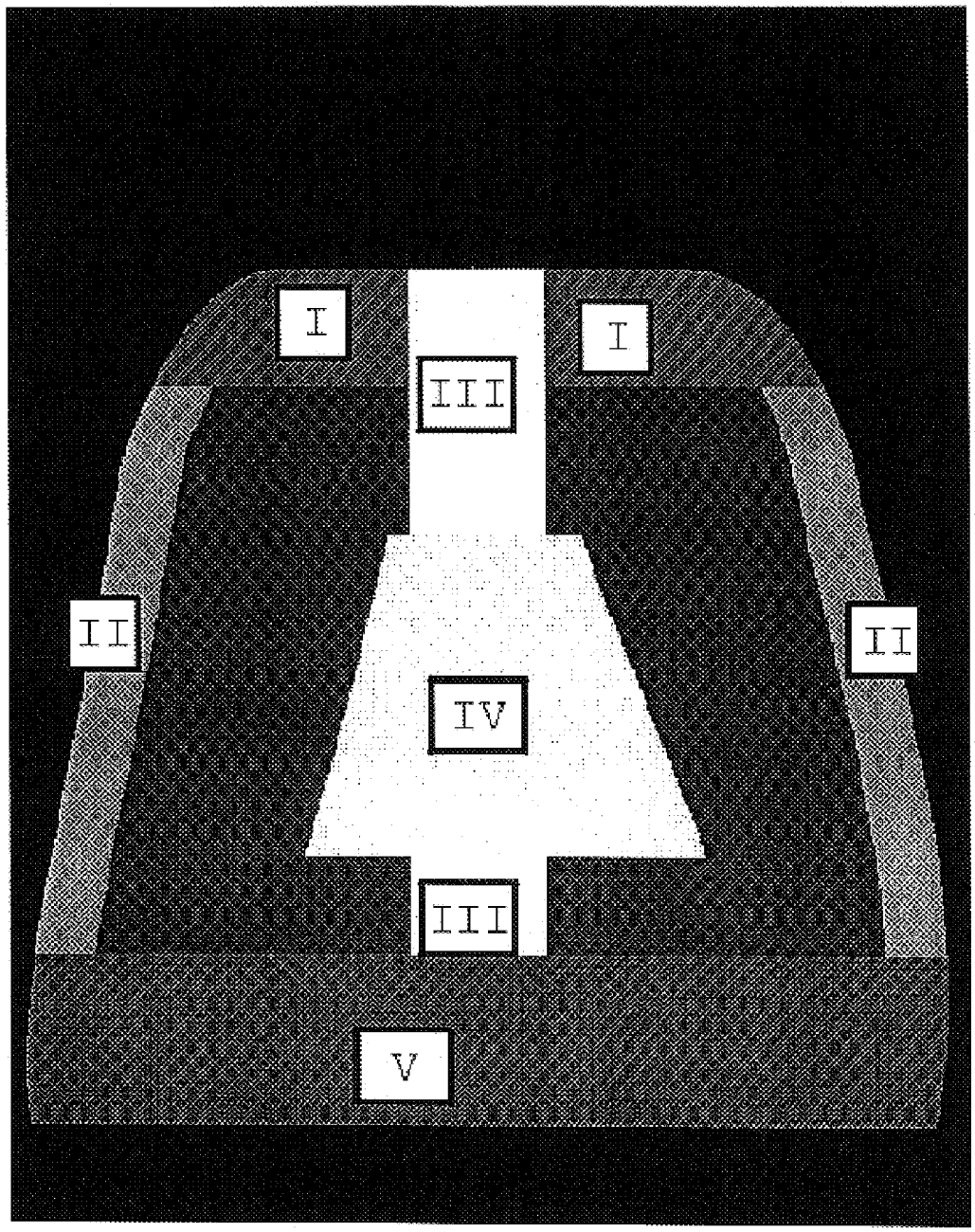
Figure 10.A

METHOD AND SYSTEM FOR THE DETECTION OF LUNG NODULE IN RADIOLOGICAL IMAGES USING DIGITAL IMAGE PROCESSING AND ARTIFICIAL NEURAL NETWORK

RELATED APPLICATIONS

This application is a continuation-in-part of Ser. No. 08/597,736, filed Feb. 6, 1996, herein incorporated by reference in its entirety now abandoned. This application is also related to an application Ser. No. 09/503,840 entitled, "Divide-and-Conquer Method and System for the Detection of Lung Nodules in Radiological Images," filed concurrently herewith and incorporated by reference herein.

TECHNICAL FIELD

The present invention relates to an automated method and system for digital image processing of radiologic images and, more specifically, to an automated method and system for the detection of abnormalities, like lung nodules in radiological chest images, using digital image processing and artificial neural networks.

BACKGROUND OF THE INVENTION

Lung cancer, next to heart disease, is the second highest leading cause of death in the United States. Successful detection of early-stage cancer tumors is able to increase the cure rate. Detection and diagnosis of cancerous lung nodules in chest radiographs are among the most important and difficult tasks performed by radiologists. To date, diagnosis in x-ray chest radiograph is the most important diagnostic procedure for detecting early-stage, clinically occult lung cancer. However, the radiographic miss rate for the detection of lung nodules is quite high. Observer error, which causes these lesions to be missed, may be due to the camouflaging effect of the surrounding anatomic background on the nodule of interest or to the subjective and varying decision criteria used by radiologists. Under-reading of a radiograph may be due to many other reasons, including lack of clinical data, focusing of attention on another abnormality by virtue of a specific clinical question, etc. However, most peripheral lung cancers are visible, in retrospect, on previous films. Thus, a need remains for an automated method and system for digital image processing of radiographic images to alert radiologists to the location of highly suspect lung nodules. Early radiological detection of lung nodules can significantly improve the chances of survival of lung cancer patients. Through its capability to locate the presence of nodules commonly obscured by overlying ribs, bronchi, blood vessels, and other normal anatomic structures on radiographs, the automated system and method should reduce false negative diagnosis, hence leading to earlier detection of pulmonary lung cancers and of metastatic nodules with high accuracy.

PRIOR ART

Several computer-aided diagnosis techniques using digital image processing and artificial neural networks have been described in the open literature and in patents. Of particular relevance to the present invention are the following:

U.S. Pat. No. 4,907,156 to Doi et al. describes a method for detecting and displaying abnormal anatomic regions existing in a digital X-ray image. A single projection digital X-ray image is processed to obtain signal-enhanced image data with a maximum signal-to-noise ratio (SNR) and is also processed to obtain signal-suppressed image data with a suppressed SNR. Then, difference image data are formed by subtraction of the signal-suppressed image data from the signal-enhanced image data to remove low-frequency structured anatomic background, which is basically the same in both the signal-suppressed and signal-enhanced image data. Once the structured background is removed, feature extraction is performed. For the detection of lung nodules, pixel thresholding is performed, followed by circularity and/or size testing of contiguous pixels surviving. thresholding. Threshold levels are varied, and the effect of varying the threshold on circularity and size is used to detect nodules. For the detection of mammographic microcalcifications, pixel thresholding and contiguous pixel area thresholding are performed. Clusters of suspected abnormalities are then detected. The major differences between the method and system of the present invention and the approach of Doi et. al include the use of a neural network architecture, use of a sphericity test, use of multiple anatomic categories, body part segmentation, and use of phantom nodules in the present invention to further improve the detection accuracy.

U.S. Pat. No. 5,463,548 to Asada et al. describes a system for computer-aided differential diagnosis of diseases, and in particular, computer-aided differential diagnosis using neural networks. A first design of the neural network distinguishes between a plurality of interstitial lung diseases on the basis of inputted clinical parameters and radiographic information. A second design distinguishes between malignant and benign mammographic cases based upon similar inputted clinical and radiographic information. The neural networks were first trained using a database made up of hypothetical cases for each of the interstitial lung diseases and for malignant and benign cases. The performance of the neural network was evaluated using receiver operating characteristic (ROC) analysis. The decision performance of the neural network was compared to experienced radiologists and achieved a high performance comparable to that of the experienced radiologists. The neural network according to the invention can be made up of a single network or a plurality of successive or parallel networks. The neural network according to the invention can also be interfaced to a computer that provides computerized automated lung texture analysis to supply radiographic input data in an automated manner. However, Asada's method is limited to the detection of lung diseases-not including lung cancer, which presents different symptoms.

Y. S. P. Chiou, Y. M. F. Lure, and P. A. Ligomenides, "Neural Network Image Analysis and Classification in Hybrid Lung Nodule Detection (HLND) System", *Neural Networks for Processing III Proceedings of the* 1993 *IEEE-SP Workshop*, pp. 517–526. The Chiou et al. article describes a Hybrid Lung Nodule Detection (HLND) system based on artificial neural network architectures, which is developed for improving diagnostic accuracy and speed of lung cancerous pulmonary radiology. The configuration of the HLND system includes the following processing phases: (1) pre-processing to enhance the figure-background contrast; (2) quick selection of nodule suspects based upon the most pertinent feature of nodules; and (3) complete feature space determination and neural network classification of nodules. Major differences between the present invention and the Chiou et al. article are that the present invention introduces nodule phantoms, a neural network for data fusion, certain ratios between multiple anatomic categories, sphericity testing, and body part segmentation.

S. C. Lo, J. S. Lin, M. T. Freedman, and S. K. Mun, "Computer-Assisted Diagnosis of Lung Nodule Detection Using Artificial Convolution Neural Network", *Proceedings of SPIE Medical Imaging VI*, Vol. 1898, 1993. This article describes nodule detection methods using a convolutional neural network consisting of a two-dimensional connection trained with a back propagation learning algorithm, in addition to thresholding and circularity calculation, morphological operation, and a two-dimensional sphere profile matching technique. Major differences between the present invention and Lo at al. article are that the present invention introduces nodule phantoms, a neural network for data fusion, certain ratios between multiple anatomic categories, sphericity testing, and body part segmentation. The architectures used in the Lo et al. article and the present invention are significantly different.

J-S Lin, P. Ligomenides, S-C B. Lo, M. T. Freedman, S. K. Mun, "A Hybrid Neural-Digital Computer Aided Diagnosis System for Lung Nodule Detection on Digitized Chest Radiographs", *Proc. 1994 IEEE Seventh Symp. on Computer Based Medical Systems*, pp. 207–212, describes a system for the detection and classification of cancerous lung nodules utilizing image processing and neural network techniques. However, the system described in this article presents differences from the present invention similar to those between the system described in the Lo et al. 1993 article and the present invention. S. C. B. LO, S. L. A. Lou, J. S. Lin, M. T. Freedman, M. V. Chien, and S. K. Mun, "Artificial Convolution Neural Network Techniques and Applications for Lung Nodule Detection", *IEEE Transactions on Medical Imaging*, 1995, Vol. 14, No. 4, pp 5 711–718, describes a system for detection and classification of lung nodules using a convolutional neural network. However, the system described in this article presents differences from the present invention similar to those between the system described in the Lo et al. 1993 article and the present invention.

M. L. Giger, "Computerized Scheme for the Detection of Pulmonary Nodules", *Image Processing VI, IEEE Engineering in Medicine & Biology Society, 11th Annual International Conference* (1989), describes a computerized method to detect locations of lung nodules in digital chest images. The method is based on a difference-image approach and various feature-extraction techniques, including a growth test, a slope test, and a profile test. The aim of the detection scheme is to direct the radiologist's attention to locations in an image that may contain a pulmonary nodule, in order to improve the detection performance of the radiologist. However, the system described in this article presents differences from the present invention similar to those between the system described in U.S. Pat. No. 4,907,156 to Doi et al. and the present invention.

SUMMARY OF THE INVENTION

The present invention for detection of abnormalities, like lung nodules, in a radiological chest image overcomes the foregoing and other problems associated with the prior art by utilizing multiple steps of digital image processing to enhance object-to-background contrast and select nodule suspects. It further uses feature extraction and neural network techniques to finally classify the suspect regions to maximize the detection of true nodules within a radiological image. Once image data is acquired from a radiological chest image, the data is subject to multiple phases of digital image processing to initially identify several suspect regions. First, during an image enhancement phase, object-to-background contrast of the data is enhanced using median and match filtering with a three-dimensional nodule phantom, which involves sorting, determination of median value, fast Fourier transformation, matrix conjugation, and multiplication. Next, during a suspect selection phase, the data is subjected to body part segmentation, morphological filtering, and sphericity testing, involving examination of shape characteristics of suspects represented as circularity parameters of each grown region in a sliced (thresholding) image obtained from a detected blob and segmentation of suspect object blocks to preliminarily select nodule candidates. In a final digital imaging phase, the classification phase, the data is first analyzed using background correction, followed by an edge operation, histogram generation, marginal distribution generation, standardization, and neural network classification and integration. Seven different anatomic structures, including rib crossing, rib-vessel crossing, end vessel, vessel cluster, rib edge, vessel, and bone (which may cause false positive detection) as well as true nodule are used as training classes to develop a neural network classifier. The use of these multiple phases and detailed categories of anatomic structures serves to eliminate a high number of false positives that result from prior art methods and to increase the detection accuracy.

In one preferred embodiment, the invention includes a system combining a computer, a video display, a scanning device and an optional X-ray lightbox in a single compact unit.

BRIEF DESCRIPTION OF THE DRAWINGS

For a greater understanding of the present invention and of the advantages thereof, reference is now made to the following description taken in conjunction with the accompanying drawings, in which:

FIG. 7 is a table demonstrating eight different anatomic structures for elimination of false positives;

FIG. 10A shows an example of dividing the lung area into five zones (I, II, III, IV, and V), each zone being represented by a different constant gray value.

DETAILED DESCRIPTION OF THE DRAWINGS

Figure 1:
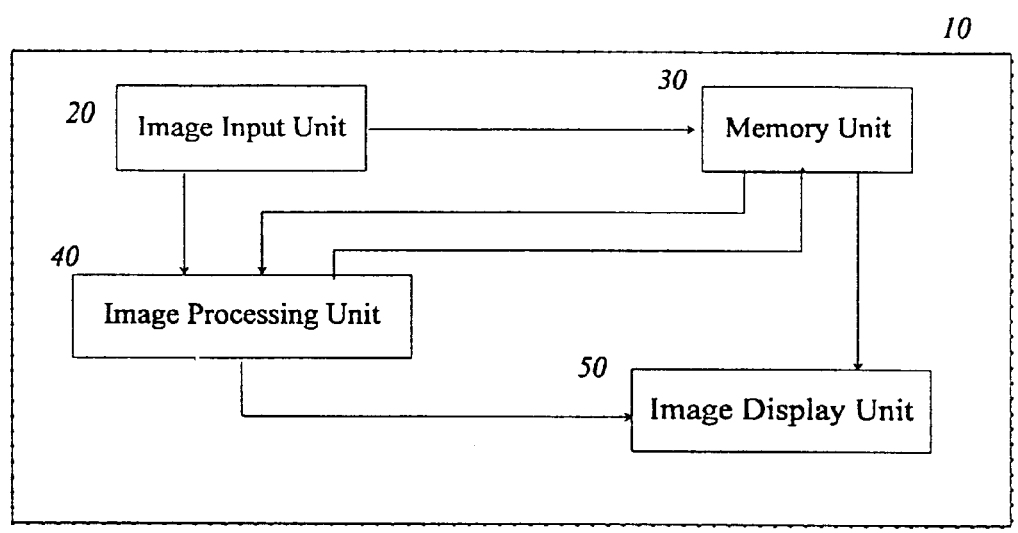
FIG. 1 illustrates a system for implementing the method of the present invention.

Referring to FIG. 1, a schematic block diagram illustrating a system for implementing the automated method and system according to an embodiment of the present invention, image data of the anatomic region of interest (e.g., a chest) is entered into the image input unit 20. For example, a video camera, computer radiography (CR) system, or a film digitizer may provide such image data. The data in the image input unit 20 is stored for later retrieval and use in the memory unit 30 or is sent to image processing unit 40. Any suitable memory unit device, such as magnetic tape, computer disk, optical laser storage, etc., can be utilized. In the image processing unit 40, the method of the present invention is applied to the image to detect lung nodules within image. The image processing unit 40 comprises three phases that correspond to the three main steps of the method of the present invention. Subsequently, the image is sent to the memory unit 30 for storage and/or an image display unit 50, such as monitor, a printer, plotter, chart recorder, or the like.

Figure 2:
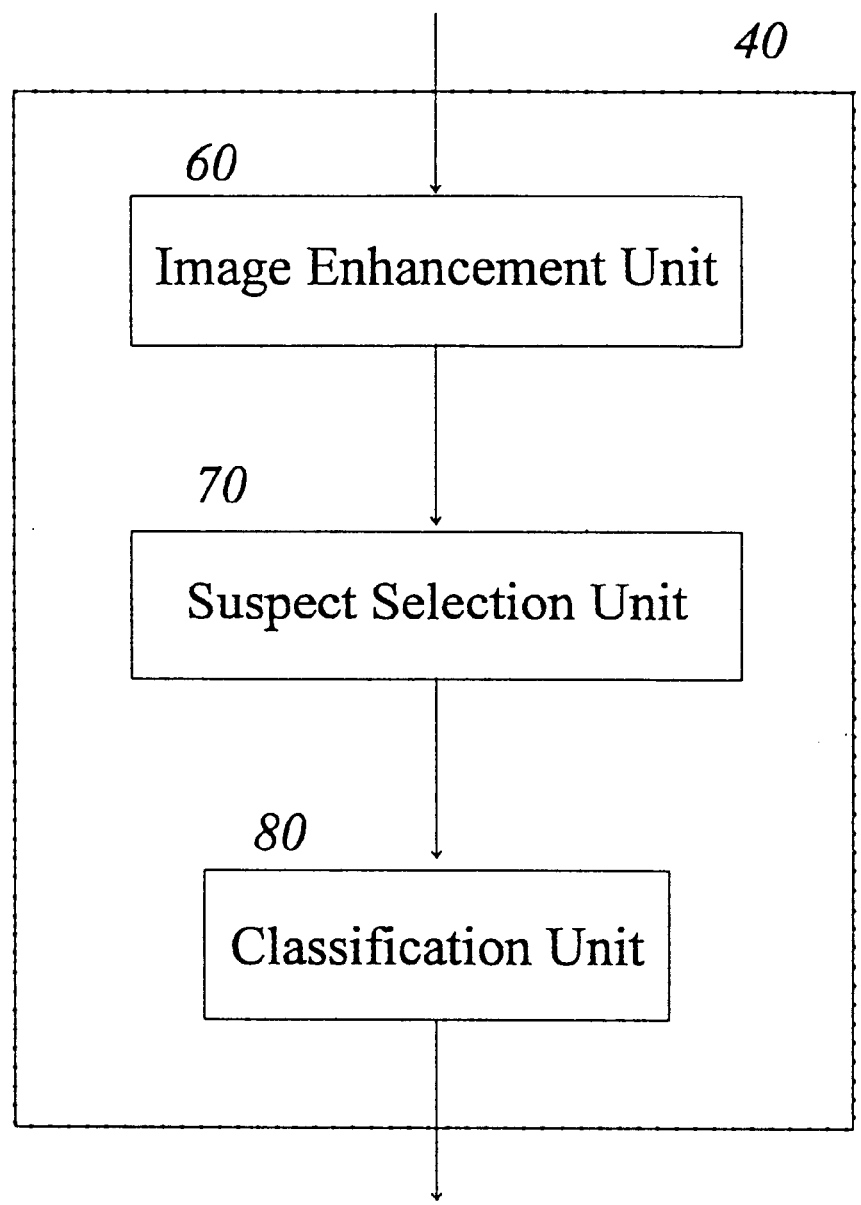
FIG. 2 is a schematic diagram of a method according to an embodiment of the present invention.

FIG. 2 illustrates a schematic diagram of the automated method and system of image processing unit 40 according to an embodiment of the present invention. The automated method and system include three phases or stages. In the first phase, an image enhancement unit 60, pixel sorting within region of interest (ROI), determination of median pixel, updating pixel value, fast Fourier transform (FFT), matrix multiplication, matrix conjugation, inverse FFT, and image subtraction are performed on the image data to enhance object-to-background contrast based on the nodule phantom. Next, during the suspect selection unit 70, body part segmentation, morphological filtering, evaluation of shape characteristics of nodule suspects with sphericity testing (involving examination of circularity parameters of each grown region in a sliced thresholding image), and image block segmentation occur to subtract unwanted image data preliminarily identified potentials area (32×32 pixels), including abnormalities (nodules). Each potential area (32×32 pixels) corresponds to a suspect area at each location on the image. Finally, during the classification unit 80, background correction, edge operation, histogram generation, marginal distribution generation, standardization, and neural network classification and integration are developed and employed to detect true and false positive categories. The location, region, and existence of true lung nodules in the image are the output of this system.

A more detailed description of each processing unit follows.

Image Enhancement Unit (step 60)

Figure 3:
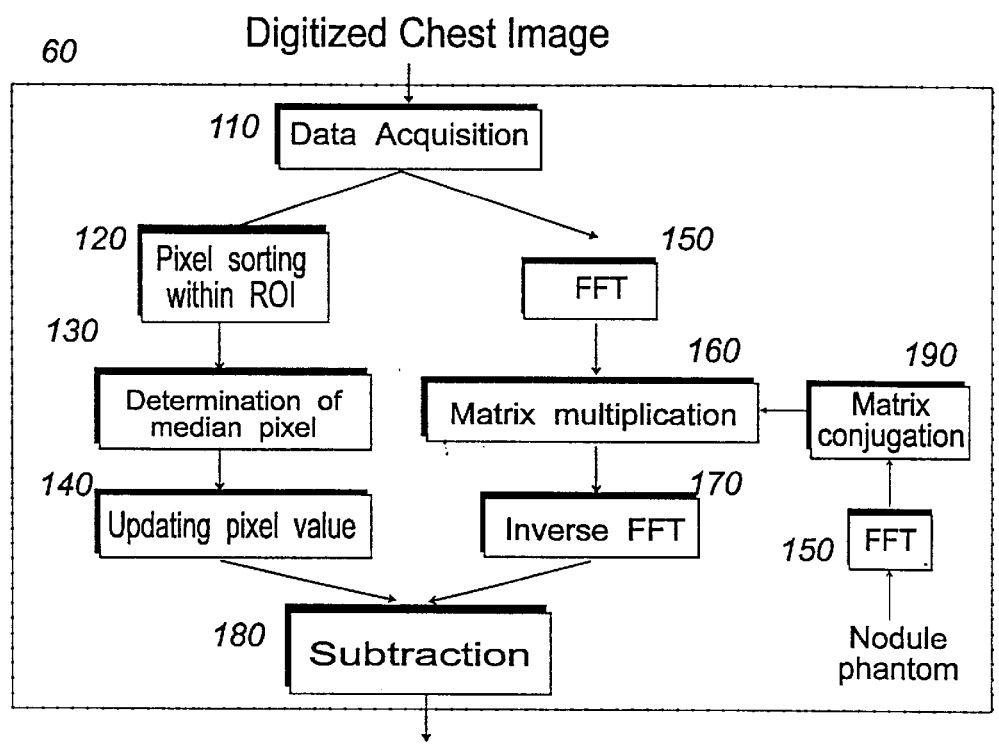
FIG. 3 is a schematic diagram of an image enhancement unit according to an embodiment of the present invention.

As shown in FIG. 3, a digitized chest image is fed into a data acquisition unit (step 110) forming part of image enhancement unit 60. While digital radiographs are becoming more readily available, typically, chest images are obtained with film-screen (x-ray) technology. In the event an x-ray film is presented for automated processing, a digitized chest image is acquired by digitizing clinical x-ray chest films or through use of a Computer Radiography (CR) system. Digital chest images possessing pixels in approximately the 100–200 $\mu$m resolution range and having 4096 gray scale levels are first acquired. A simple contrast scaling function, like window leveling, is used to obtain a constant contrast between the lung space area and the mediastinum area. Each pulmonary image is subsequently to be reduced to 500×512×12 bits (by averaging a 2×2 pixel region) for use with the automated method and system of the present invention and is routinely obtained using the foregoing techniques.

The image acquired is simultaneously processed using SNR suppression median (step 120, 130, and 140) and SNR enhancement matched (step 150, 160, and 170) filtering techniques. The SNR suppression median filtering technique typically involves pixel sorting within a region of interest (ROI; i.e., pixel sorting within ROI 120), determination of median pixel (step 130), and updating pixel value (step 140). A circular region 3 mm in diameter is used for each ROI in step 120. All the pixel values inside an ROI are sorted to generate a cumulative distribution function (CDF), and the middle value (the median value in the CDF) is determined in step 130. The middle value is then used to replace the central pixel of the ROI in step 140. The same procedure is applied to the adjacent pixel until entire image is processed. The median filtering technique can also be implemented in another way by updating the CDF instead of re-generating a new CDF from the ROI corresponding to the adjacent pixel. This technique tends to smooth the image by reducing the intensity of abnormal phenomena, e.g., nodules. The SNR enhancement matched filtering technique typically involves fast Fourier transformation (FFT; step 150), matrix multiplication (step 160), inverse FFT (step 170), and matrix conjugation (step 190) to correlate the energy of a nodule phantom with an original image. A spherical profile with a diameter of 3 mm as well as contrast between the center of a nodule phantom and its border are used to synthesize the ideal nodule image along with its surrounding anatomic background for the nodule phantom. Such a nodule phantom contains information of a typical nodule and its neighborhood. The nodule phantom image is subsequently processed with an FFT 150, followed by a matrix conjugation operation 190. The image from step 190 can also be stored in the memory for fast processing. This technique generates resultant images with highest values corresponding to the locations of potential nodule suspects. The matched filtering techniques can also include different variations, such as spatial correlation between an original and a phantom image, the use of different fast Fourier transform techniques (e.g., discrete cosine transform), use of a Gaussian shape as a phantom nodule, and the like. Subtraction (step 180) between the resultant images derived from median and matched filtering techniques further enhances the nodule-to-background contrast. The difference image, containing nodule-enhanced signal, is used in the suspect selection unit (step 70).

Suspect Selection Unit (step 70)

Figure 4:
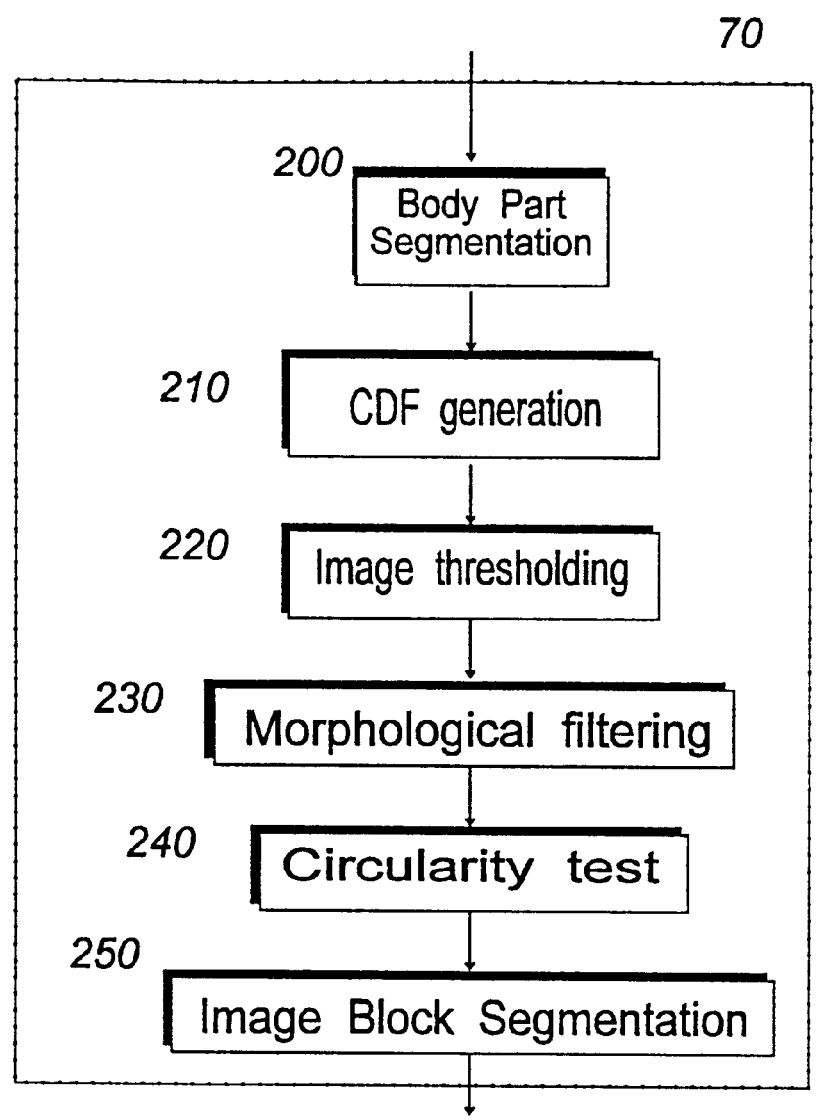
FIG. 4 is a schematic diagram of a suspect selection unit according to an embodiment of the present invention.

FIG. 4 shows an embodiment of the suspect selection unit 70 of the image processing unit 40 illustrated in FIG. 2. This processing phase is primarily based on a typical nodule shape—spherical shape. Body part segmentation (step 200) includes external-lung-region segmentation and internal-lung-region segmentation. The external- lung-region segmentation limits the detection of lung nodules inside the found lung area whereas the internal-lung-region segmentation ensures that both nodules and false positives in different zones are processed differently and separately in order to increase the sensitivity. The external-lung-region segmentation is first applied to the original data to identify the chest region by excluding the outside lung area. This is accomplished by eliminating pixels with code values in the lowest 5% of the histogram of the entire difference image in order to reduce any potential for false detection of outside body parts. Such image pixel values in the lowest 5% correspond to the region outside the chest region. In body part segmentation (step 200), internal-lung-region segmentation also segments the chest region into different anatomic regions based on the existence of nodule and anatomic structures detected by the current method.

Figure 10B:
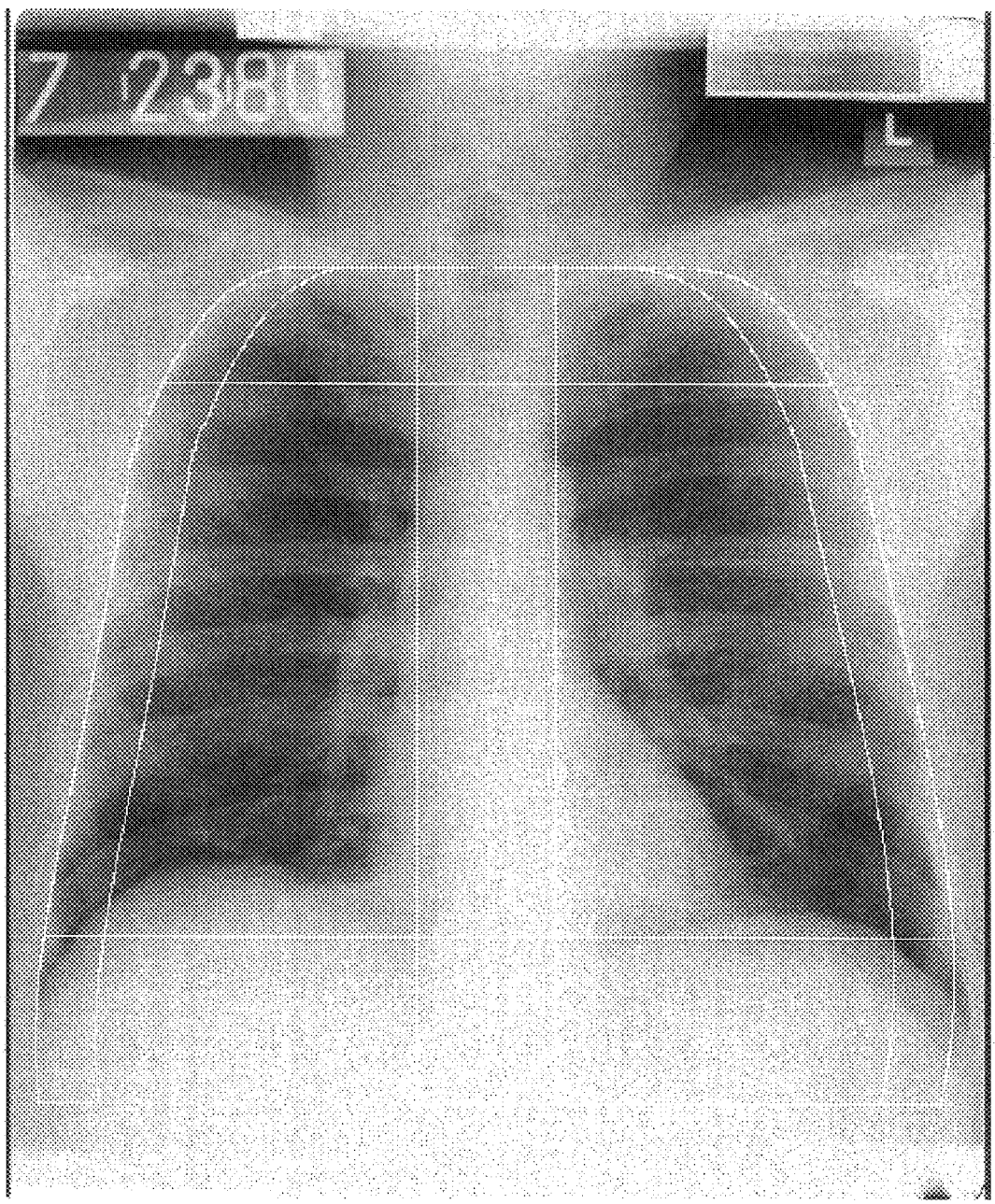
FIG. 10B shows an example of an original image overlaid with zone contours.

FIGS. 10A and 10B show an example of internal-lung-region segmentation in the body part segmentation (step 200). Internal-lung-region segmentation segments the lung area into different overlapped zones of similar anatomic structure and image characteristics. The lung area is segmented into different overlapped zones, such as clavicle (ZONE I), peripheral edge (ZONE II), spine (ZONE III), heart (ZONE IV), and mediastinum (ZONE V) zones. Such segmentation allows: (1) the application of different image processing techniques to enhance the nodule signal and search the nodule candidates; (2) design of different expert classifiers for each zone based on image characteristics in each zone; and (3) optimal combination of nodule candidates based on the performance (sensitivity and specificity) of each classifier for each zone.

A sphericity test is then performed by examining the circularity parameters of grown regions located at the same coordinates in different sliced threshold images. The method is described as follows. First, a cumulative distribution function (CDF) is generated (step 210) for an entire difference image except the boundary region with a width of 32 pixels. Ten different code values are selected as threshold values, based on their corresponding probabilities in the CDF (typically code values corresponding to 95%, 90%, 85%, etc., of CDFs), to generate 10 different binary thresholding images with a code value 1 indicating that a given pixel in different images is greater than the threshold value (step 220). Slicing the image containing detected blobs into 10 different thresholding binary images (sliced thresholding images) permits analyzing a 3-D sphere as several 2-D circles with different sizes at same location. Measurement of circularity of the set of circles against a set of pre-determined criteria gives an indication of the location and size of a nodule suspect. Each sliced thresholding image is further processed with morphological filtering (step 230), in a preferred embodiment, a sequence of erosion followed by dilation by using a 3-mm diameter circular kernel. Here both erosion (e) and dilation (d) are defined as:

$$e = \min\{I_{i,j}\}, \tag{1}$$

$$d = \max[I_{i,j}], \forall\ (i^2 + j^2)^{1/2} < (d/2), \tag{2}$$

where d is the diameter of circular kernel. The matrix I corresponds to pixel values of the digital input image. Such morphological filtering is used to eliminate the presence of small vascular structures while retaining the relatively large structures of ribs and nodules. Several isolated islands (grown region) are then formed in each thresholding image. As the threshold value increases, the grown region becomes smaller. The grown regions of different thresholding images exist in the same locations. By combining these thresholding images, a blob can be detected for each nodule suspect.

Figure 5:
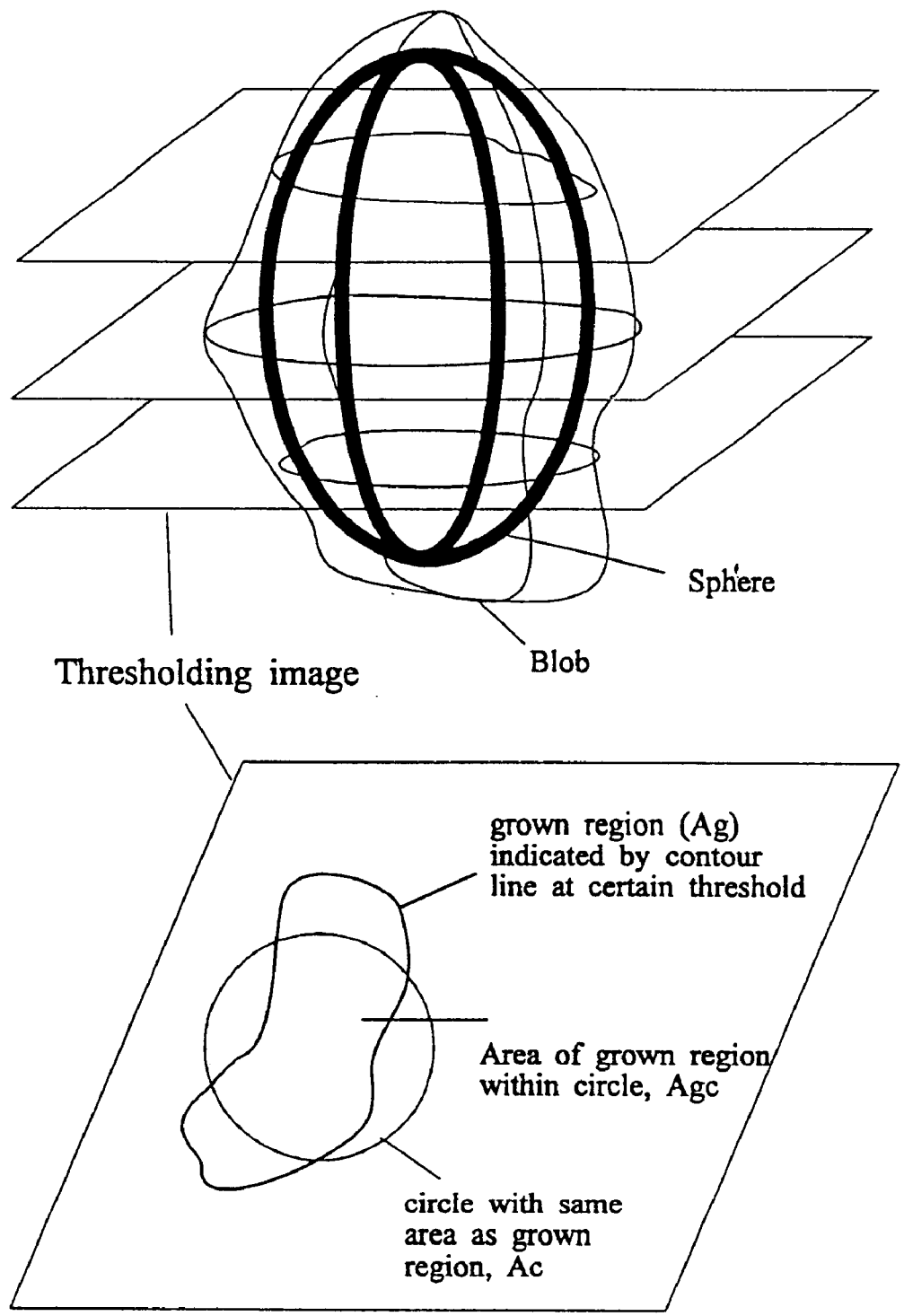
FIG. 5 illustrates the detected blob and grown region at thresholding image of a lung nodule suspect.

FIG. 5 illustrates the detected blob and grown region of a thresholding image of a lung nodule suspect for circularity test. A circularity test procedure (step 240) is performed on each thresholding image by examining several parameters, including effective radius (r), circularity (C), and irregularity (Ir) at certain contour lines of the grown region of each thresholding binary image. These terms are defined as:

$$r = \sqrt{\left(\frac{A_g}{\pi}\right)} \tag{3}$$

$$C = \frac{A_{gc}}{A_g} \tag{4}$$

$$I_r = \frac{P_c}{P_g} \tag{5}$$

where Ag denotes area of a grown region, Agc denotes area of the grown region within a circle (which has same area as the grown region), Pc denotes the perimeter of the circle, and Pg denotes the perimeter of the grown region. Regions at the same location are selected as nodule candidates if the tests for r, C, and Ir of the grown region are met within pre-defined thresholds for at least 7 out of 10 sliced thresholding images. Choosing regions at the same location for 7 sliced thresholding images instead of in different locations allows more accurate characterization of the true nodule shape, i.e., a sphere instead of a circle. The selected nodule candidates are then segmented into, typically, 32×32 image blocks, or approximately 9 mm² areas (step 250), centered at the suspect candidate regions for the final classification in step 80. After the first two processing phases (image enhancement and suspect selection) on a set of radiographs, many nodule suspects in original and difference image blocks (32×32 pixel) are obtained for further development via artificial neural network (ANN) classification. The suspect image blocks are classified into several anatomic structures in order to determine false positives during the classification unit.

FIG. 7 shows a table demonstrating eight different anatomic structures for the feature extraction and neural network classification. They include true nodule (TN), rib crossing (RX), rib-vessel crossing (RV), vessel cluster (VC), end-vessel (EV), rib edge (RE), bone (BO), and vessel (VS), confirmed by CT and a radiologist for the training and development of a neural network classifier, or any classifier. The latter seven structures are all false positive structures to be weeded out during classification. The number of each anatomic structure is different due to the performance of image enhancement unit (step 60) and suspect selection unit (step 70). The ratio among the true nodule and other anatomic structures is generally the same, however, regardless of the input images. For example, the ratio for RX, RV, VC, EV, VS, RE, and BO are 10: 10 : 5 : 10 : 4: 1: 1. However, in different zones, these ratios may, alternatively, have different predetermined values. The advantage of using multiple category classification is that it facilitates the training of the neural networks to distinguish the subtle differences between nodules and the anatomic structures.

Classification Unit (step 80)

Figure 6:
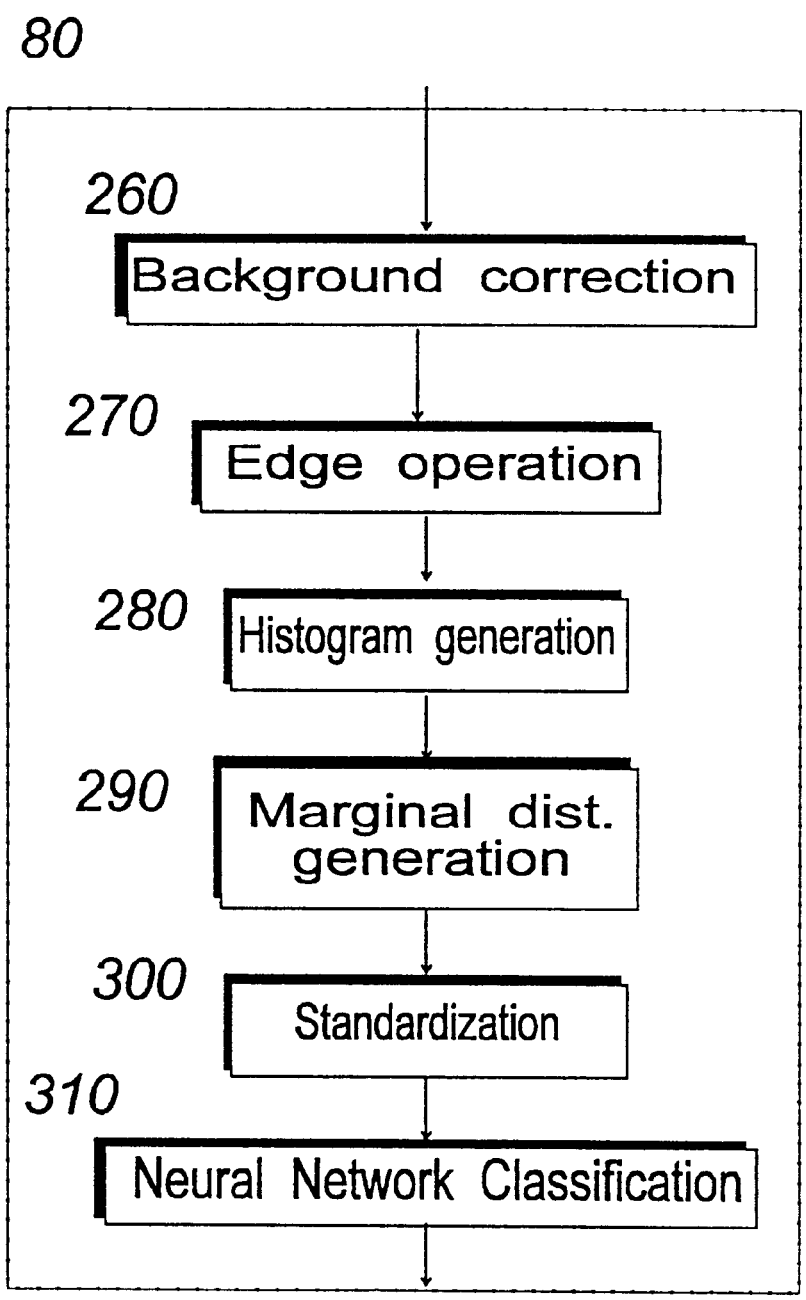
FIG. 6 is a schematic diagram of a classification unit according to an embodiment of the present invention.

As referred to in FIG. 6, an algorithm based on localized anatomic features is applied for feature extraction and neural classification on 32×32 image blocks. A segmented image block (32×32 pixels) is first processed via a background correction process (step 260), which fits the image block with a two-dimensional second order polynomial function. The fitted image is then processed with an edge operation (step 270), for example, a 3×3 Sobel edge operator, to obtain two edge maps: amplitude and orientation. The orientation angles are within the range between 0 and 360 degrees, whereas the amplitude varies from 0 to 1024. A two-dimensional histogram for both amplitude and orientation is then generated in the histogram generation processing (step 280), because the different anatomic structures clearly show different behaviors in such a two-dimensional histogram. It is found that for true nodules the distribution of orientation angles is relatively uniform compared with other false positive cases, and the magnitude of gradient amplitude of true nodules is mostly concentrated in the smaller magnitudes. Most types of false positive nodules demonstrate two peaks separated at around 180 degrees in orientation angle axis, except for vessel clusters. Because bone is wider than vessels in the 32×32 images and the contrast between bone and anatomic background is stronger than that for vessels, one peak in the distribution of orientation is typically smaller than another one for bone, whereas they are within a similar range for the vessel class. Each peak in bone gradient images is sharper (i.e., smaller standard deviation) than those in vessel images. A rib-edge gradient image shows one stronger amplitude distribution at a certain angle because of the orientation of the rib in the 32×32 image. A gradient distribution for a rib-vessel crossing also demonstrates one stronger peak with relatively larger standard deviation at an orientation axis. In other words, the orientation information is more dominant than amplitude information for this category. Although one expects to obtain one sharper peak in the angle axis, it shows very insignificant effect due to the low contrast of an end vessel. A vessel-cluster gradient image shows a rougher contour (i.e., larger standard deviation along the amplitude axis) than that of a nodule. This type of analysis and classification algorithm performs well in noisy conditions because the distribution enhancement tends to smooth out the noise contribution to the feature vector.

By integrating the two-dimensional histogram with respect to amplitude and orientation in the marginal distribution generation process (step 290), two sets of marginal distribution curves are obtained: one for orientation distribution and another one for amplitude distribution, each of which contains 32 elements (bins). The integration of amplitude and orientation information is normally called data fusion processing, and it allows the more reliable feature of the input features (either amplitude information or orientation information) to dominate the most prominent characteristics (as described above). Each distribution is normalized to enhance its variation by performing division of ten, which is the deviation of these curves, followed by taking its square in the standardization processing (step 300). A supervised back-propagation (BP) neural network classifier is developed for detection of each anatomic structure (step 310).

Figure 8:
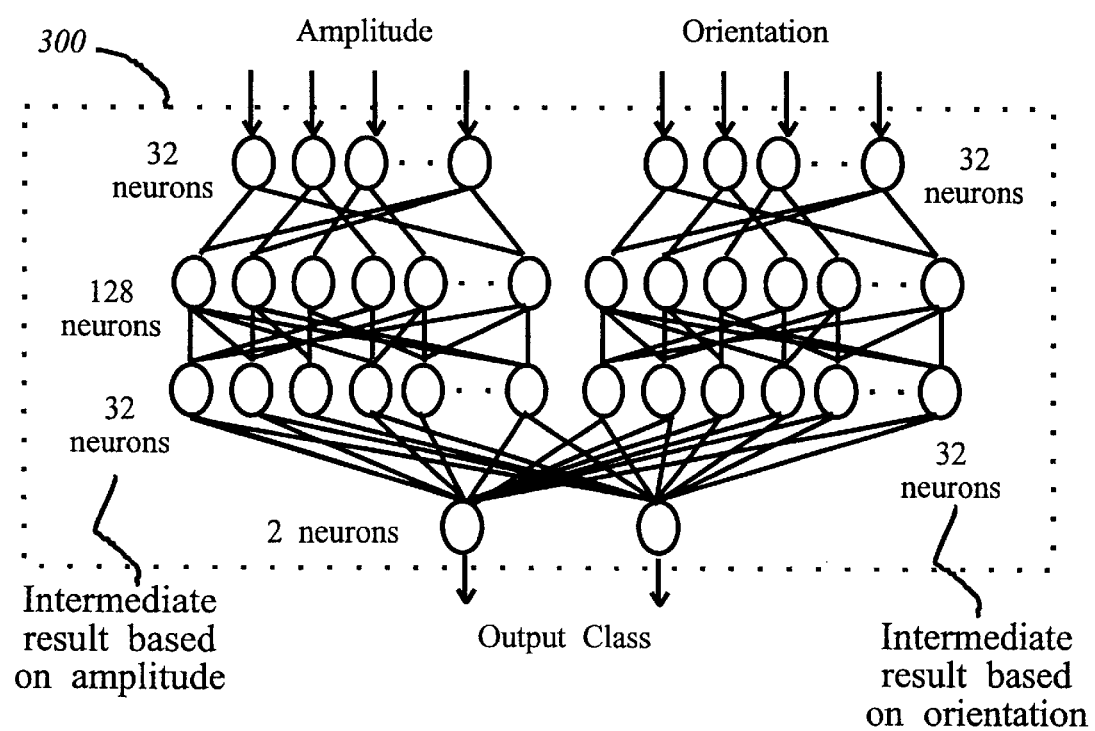
FIG. 8 demonstrates the architecture of a back propagation trained feed forward neural network classifier used in the automated method and system of an embodiment of the present invention.

As shown in FIG. 8, the back propagation (BP) artificial neural network (ANN) classifier contains four processing layers. An input layer consists of 64 neurons corresponding to combination of both amplitude and orientation bins of the marginal distribution. Each of two sets of (amplitude and orientation bins) neurons in the input layer performs the computation based on each individual feature set. Hence, each set of neurons works as an individual classifier. Two hidden layers contain 128 and 64 neurons, respectively, which are chosen as multiples of eight (i.e., the number of pre-determined anatomic structure classes shown in FIG. 7, since the properties of each class are desired to be coded evenly within the network). It is intended that two hidden layers will extract the curvilinear features and grasp the joint behaviors of the distributions. The grasping of the joining behaviors is the resultant performance of integration of each individual classifier in the input layer. The integration processing is usually called data fusion. Finally a two-neuron output layer is used to classify either TRUE positive or FALSE positive nodules. A sigmoidal transfer function, varying from −1 to +1, is used as activation function in each neuron. Furthermore, a two hidden-layer BP ANN with sigmoidal nonlinearities has been demonstrated theoretically and experimentally to classify any shape of decision region and to approximate complex nonlinear functions.

The data set of 32×32 image blocks containing various anatomic classes is first separated into a training set and a test set. The BP ANN learns from the training set presented to it during a learning phase (weight adaptation); this phase continues until most of the training cases are learned properly. The trained network is then applied to the test data set. Approximately 40% of the data set is used as training examples, and the rest of them are used as a test set. Since the BP ANN learns from the training data set presented to it during a learning phase (weight adaptation phase), the training samples need to be distributed equally among classes. By so doing, the BP ANN will not be biased toward any result classes (in this case, TRUE nodule class and FALSE nodule class).

In building a data set, a TRUE nodule sample was replicated several times, and FALSE nodule samples were duplicated based upon the statistical properties of the training set such that there were similar amounts of TRUE and FALSE positive samples in the training sample set. In one test, it took approximately 150 iterations to train the BP ANN classifier to learn up to 100% accuracy based on the training samples.

After training of the neural network is complete, entire data sets are then applied to the network to generate output values ranging from −1 to +1 at each neuron, representing the possibilities of the occurrences of TRUE and FALSE nodules.

Such a neural network architecture 300, consisting of two classifiers of two sets of input neurons and hidden layers, works as a data fusion center that integrates the detection results from different classifiers to arrive at an optimal detection result. The first 32 input neurons receive classification results from one classifier, and the last 32 input neurons receive classification results from another classifier. Both classifiers are not fully correlated. The number of input neurons changes based upon the number of classifiers and their classification results. The architecture of the neural network is designed based on the performance of each individual classifier. The input and output neurons are determined from the number of classifiers and desired output classes, respectively. The weights or connections of the neural net are evaluated based on the likelihood ratio to initialize the confidence levels for different classifiers. This neural network is further trained with sample data. Such a neural network is very easy to implement in a hardware platform.

The automated system and method for lung nodule detection has been implemented for both automatically and interactively processing digitized images. An automated procedure reads input image, performs detection, and prints out the location of nodule suspects as well as corresponding 32×32 image blocks in both original and difference formats without supervision. An interactive procedure on a mouse-based window system using MS-DOS Graphic User Interface (GUI) implementation has been demonstrated. The GUI was designed specifically for medical image processing and detection. A user can click at on-screen mouse buttons for image display, zooming of nodule suspects, image enhancement, size and location, suspect image block display in original form or in subtract form. The suspected nodules are identified as circles, with their radii identical to their equi-area radii. The system also provides an image coordination indicator to easily locate the suspect image blocks in the x-ray film.

Figure 9:
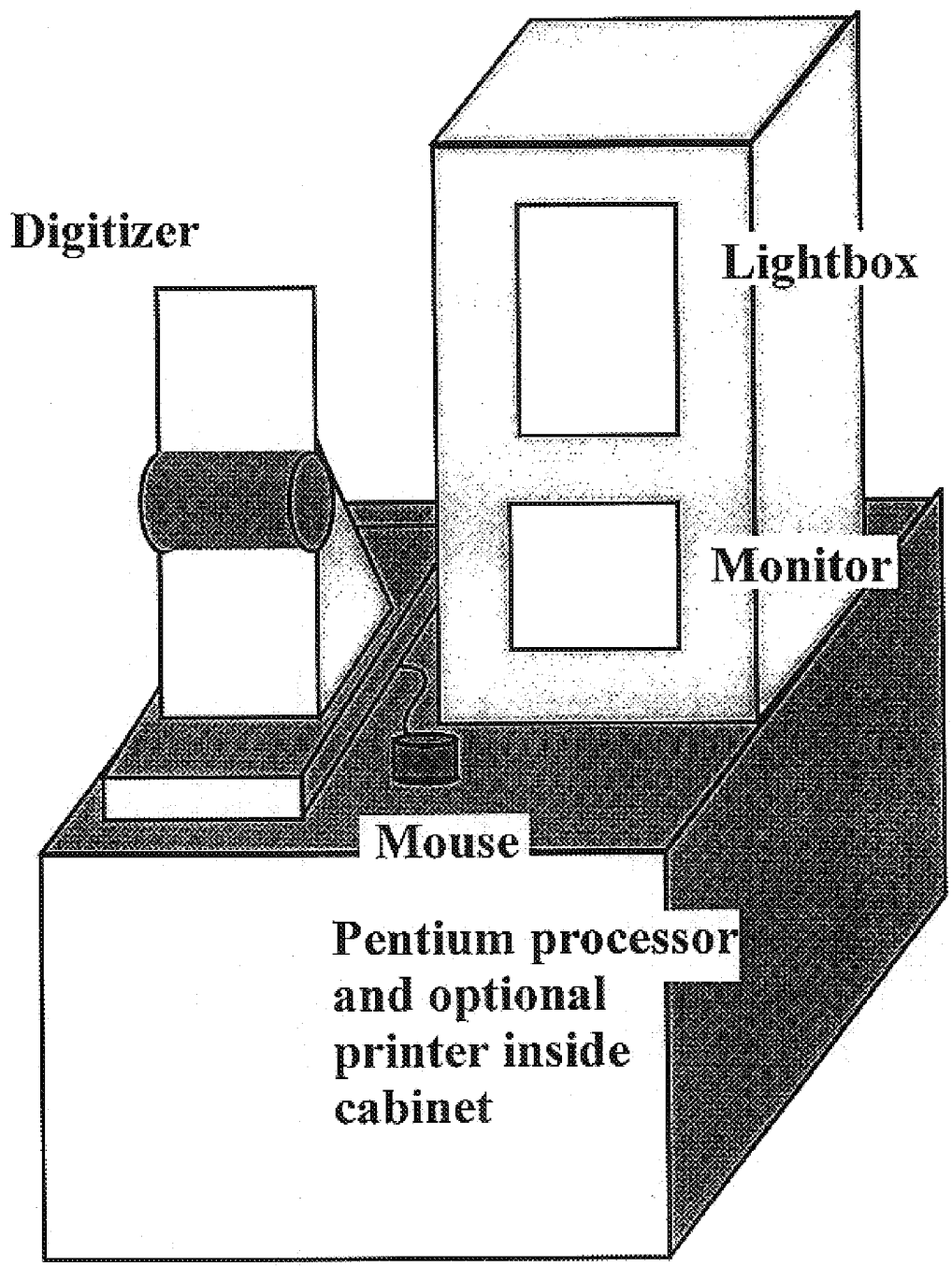
FIG. 9 is a representation of a unit that combines the hardware components and the analysis and operational software into a single unit, according to an embodiment of the present invention.

As shown in FIG. 9, a system according to an embodiment of the invention consists of an enclosure housing several components to accomplish all functions in a compact space. The major hardware components include a small computer for analysis and control, a video display for display of digitized images, a pointing device, for example, a mouse, a lightbox, as well as an optional printer. Operation is as follows: A technician scans the film in, and the computer analyzes the image and finds any suspicious sites. The film and the results are then reviewed by the user, typically a radiologist. An optional printer can provide a representation of the image with the suspect areas identified.

It should be understood that the methods and systems described herein may be modified within the scope of the invention. For example, while the inventive methods and systems are described herein in connection with the detection of lung nodules, it should be clear that these methods and systems may be used for detecting other types of cancer, such as microcalcification clusters or masses in breast cancer, nodules, lumps, irregularities, or tumors in other body parts.

We claim:

1. A method for detecting an abnormality in a radiological image, the method comprising the steps of:

image enhancement processing to enhance contrast between an abnormality and the background using a phantom of an abnormality;

suspect selection processing to preliminarily select a suspected abnormality based on shape characteristics of such an abnormality, said suspect selection processing including a step of body part segmentation, which includes a sub-step of differentiation of different zones within a lung region of said radiological image;

neural network classification and integration processing to determine a presence and a location of an abnormality, and for identifying a false abnormality; and segmenting the lung region into different zones based on anatomic structures of the lung region and on local image characteristics;

wherein said neural network classification and integration processing includes the steps of:

using a different neural network classifier for each of said zones, the particular classifier for a particular zone taking advantage of the characteristics of the particular zone; and optimally combining nodule candidates based on the performances of the various classifiers for the various zones.

2. A method according to claim 1, wherein nodule candidates inside the same zone are clustered together.

3. A method according to claim 1, wherein said step of optimally combining nodule candidates is based on the different sensitivity and specificity performances of the different classifiers.

4. A method as claimed in claim 1, said classification processing further including step of:

separating anatomic structures into at least two of the following categories: Rib-Crossing (RX), Rib-Vessel Crossing (RV), Vessel Cluster (VC), End Vessel (EV), Rib Edge (RE), Bone (BO), and Vessel (VS).

5. A method according to claim 1, said image enhancement processing comprising the steps of:

receiving a nodule phantom; and performing a matched filtering operation using said nodule phantom, the matched filtering operation being used to enhance contrast between an abnormality and background.

6. A method according to claim 5, wherein said nodule phantom is a three-dimensional simulation of a nodule and its surrounding background.

7. A method according to claim 1, said suspect selection processing including said body part segmentation, and said body part segmentation including steps of:

discarding image pixels that correspond to regions outside a chest in said radiological image.

8. A method according to claim 1, wherein said different zones include clavicle, peripheral edge, spine, heart, and mediastinum.

9. A method according to claim 1, said step of neural network classification and integration processing including the steps of:

using a different neural network classifier for each of said zones, the particular classifier for a particular zone taking advantage of the characteristics of the particular zone; and optimally combining nodule candidates based on the performances of the various classifiers for the various zones.

10. A method according to claim 9, wherein nodule candidates inside the same zone are clustered together.

11. A method according to claims 9, wherein said step of optimally combining nodule candidates is based on the different sensitivity and specificity performances of the different classifiers.

12. A method according to claim 1, said suspect selection processing including the step of comparing one or more measured parameters to corresponding parameters of said phantom.

13. A method according to claim 1, said neural network classification including the step of inputting a data set into a neural network for training said neural network classification process, said data set based on edge features of said abnormality and on anatomic structures.

14. A method according to claim 1, said neural network classification processing including the step of performing fusion processing.

15. A method according to claim 14, said fusion processing including the step of integrating classification results from two or more classifiers.

16. A method for detecting an abnormality in a radiological image, the method comprising the steps of:

image enhancement processing to enhance contrast between an abnormality and the background using a phantom of an abnormality;

suspect selection processing to preliminarily select a suspected abnormality based on shape characteristics of such an abnormality, said suspect selection processing including a step of body part segmentation, which includes a sub-step of differentiation of different zones within a lung region of said radiological image;

neural network classification and integration processing to determine a presence and a location of an abnormality, and for identifying a false abnormality; and segmenting the lung region into different zones based on anatomic structures of the lung region and on local image characteristics;

wherein said different zones overlap each other.

17. A method according to claim 16, said image enhancement processing comprising the steps of:

receiving a nodule phantom; and performing a matched filtering operation using said nodule phantom, the matched filtering operation being used to enhance contrast between an abnormality and background.

18. A method according to claim 17, wherein said nodule phantom is a three-dimensional simulation of a nodule and its surrounding background.

19. A method according to claim 16, said suspect selection processing further comprising at least one of the following functions based on said shape characteristics of an abnormality: cumulative distribution function generation, image thresholding, morphological filtering, sphericity testing, and image block segmentation; and wherein said shape characteristics correspond to a spherical shape.

20. A method according to claim 16, wherein the different zones include the clavicle, peripheral edge, spine, heart and mediastinum.

21. A method according to claim 16, wherein said suspect selection process comprises the step of:

comparing one or more measured parameters to corresponding parameters of said phantom in said different zones inside the lung region.

22. A method according to claim 16, said neural network classification processing comprising the step of:

performing neural network classification of said abnormality in said different zones within the lung region.

23. A method according to claim 22, the step of performing neural network classification further comprising the step of:

for each of said different zones within the lung region, using neural network classification that is tailored to the particular zone.

24. A method according to claim 22, the step of neural network classification includes the step of:

inputting a data set into a neural network for training said neural network classification process, said data set based on edge features of said abnormality and on anatomic structures.

25. A method according to claim 16, said classification processing further includes the step of:

separating anatomic structures into at least two of the following categories: Rib-Crossing (RX), Rib-Vessel Crossing (RV), Vessel Cluster (VC), End Vessel (EV), Rib Edge (RE), Bone (BO), and Vessel (VS).

26. A method according to claim 16, said neural network classification processing including the step of performing fusion processing in different zones within the lung region.

27. A method according to claim 26, said fusion processing including the step of integrating classification results from two or more classifiers.

28. A method according to claim 16, said suspect selection processing including steps of:

image thresholding to obtain a set of sliced threshold images; and sphericity testing, the sphericity testing being performed on the same location in each one of the sliced threshold images.

29. A system for detecting an abnormality in a radiological image comprising:

an image enhancement unit that enhances contrast between an abnormality and the using a phantom of an abnormality;

a suspect selection unit that preliminarily selects a suspect abnormality based on shape characteristics of such an abnormality, said suspect selection unit including:

a body part segmentation unit that differentiates different zones within the lung region of said radiological image, wherein said body part segmentation unit segments the lung region into different zones based on anatomic structures of the lung region and on local image characteristics; and a neural network classification and integration unit that determines a presence and a location of an abnormality and identifies a false abnormality, said neural network classification and integration processing unit including:

a different neural network classifier for each of said zones, the particular classifier for a given zone taking advantage of the characteristics of the particular zone; and means for optimally combining nodule candidates based on the performances of the various classifiers for the various zones.

30. A system according to claim 29, wherein nodule candidates in the same zone are clustered together.

31. A system according to claim 29, wherein said means for optimally combining nodule candidates works based on the different sensitivity and specificity performances of the different classifiers.

32. A system according to claim 29, said neural network classification and integration unit separating anatomic structures into at least two of the following categories: Rib-Crossing (RX), Rib-Vessel Crossing (RV), Vessel Cluster (VC), End Vessel (EV), Rib Edge (RE), Bone (BO), and Vessel (VS).

33. A system according to claim 29, wherein said image enhancement unit comprises a matched filtering unit that receives a nodule phantom and performs a matched filtering operation to enhance abnormality to background contrast.

34. A system according to claim 33, wherein said nodule phantom is a three-dimensional simulation of a nodule and its surrounding background.

35. A system according to claim 29, wherein said suspect selection unit further includes at least one of the following units, which perform functions based on shape characteristics of an abnormality: a body part segmentation unit, a cumulative distribution function generation unit, an image thresholding unit, a morphological filtering unit, a sphericity testing unit, and an image block segmentation unit; and wherein said shape characteristics correspond to a spherical shape.

36. A system according to claim 29, said suspect selection processing unit including said body part segmentation unit, and said body part segmentation unit discarding image pixels that correspond to regions outside a chest in said radiological image.

37. A system according to claim 36, wherein said different zones are overlapping.

38. A system according to claim 36, wherein said different zones include clavicle, peripheral edge, spine, heart, and mediastinum.

39. A system according to claim 29, said neural network classification and integration processing unit including:

a different neural network classifier for each of said zones, the particular classifier for a particular zone taking advantage of the characteristics of the particular zone; and means for optimally combining nodule candidates based on the performances of the various classifiers for the various zones.

40. A system according to claim 39, wherein nodule candidates inside the same zone are clustered together.

41. A system according to claim 39, wherein said means for optimally combining nodule candidates works based on the different sensitivity and specificity performances of the different classifiers.

42. A system according to claim 29, said suspect selection processing unit comparing one or more measured parameters to corresponding parameters of said phantom.

43. A system according to claim 29, said neural network classification and integration processing unit including a neural network, wherein the neural network is trained by inputting a data set, said data set based on edge features of said abnormality and on anatomic structures.

44. A system according to claim 29, said neural network classification and integration processing including means for performing fusion processing.

45. A system according to claim 44, said means for fusion processing integrating classification results from two or more classifiers.

46. A system for detecting an abnormality in a radiological image comprising:
- an image enhancement unit that enhances contrast between an abnormality and the using a phantom of an abnormality;
- a suspect selection unit that preliminarily selects a suspect abnormality based on shape characteristics of such an abnormality, said suspect selection unit including:
  - a body part segmentation unit that differentiates different zones within the lung region of said radiological image, wherein said body part segmentation unit segments the lung region into different zones based on anatomic structures of the lung region and on local image characteristics, wherein said different zones overlap each other; and
- a neural network classification and integration unit that determines a presence and a location of an abnormality and identifies a false abnormality.

47. A system according to claim 46, wherein said image enhancement unit comprises a matched filtering unit that receives a nodule phantom and performs a matched filtering operation to enhance abnormality to background contrast.

48. A system according to claim 47, wherein said nodule phantom is a three-dimensional simulation of a nodule and its surrounding background.

49. A system according to claim 46, wherein said suspect selection unit further includes at least one of the following units, which perform functions based on shape characteristics of an abnormality: a cumulative distribution function generation unit, an image thresholding unit, a morphological filtering unit, a sphericity testing unit, and an image block segmentation unit; and
- wherein said shape characteristics correspond to a spherical shape.

50. A system according to claim 46, wherein the different zones include clavicle, peripheral edge, spine, heart, and mediastinum.

51. A system according to claim 46, wherein said suspect selection unit compares one or more measured parameters to corresponding parameters of said nodule phantom in said different zones inside the lung region.

52. A system according to claim 46, said neural network classification and integration processing unit further comprising:
- for each of said different zones within the lung region, a neural network classification processing unit that is tailored to the particular zone.

53. A system according to claim 46, wherein said neural network classification and integration processing unit is trained by inputting a data set, said data set based on edge features of said abnormality and on anatomic structures.

54. A system according to claim 46, wherein said neural network classification and integration processing unit includes a feature extraction unit that extracts edge features of said abnormality.

55. A system according to claim 46, wherein said classification unit separates anatomic structures into at least two of the following categories: Rib-Crossing (RX), Rib-Vessel Crossing (RV), Vessel Cluster (VC), End Vessel (EV), Rib Edge (RE), Bone (BO), and Vessel (VS).

56. A system according to claim 46, wherein said neural network classification and integration processing unit performs fusion processing in different zones within the lung region.

57. A method according to claim 56, wherein said fusion processing integrates classification results from two or more classifiers.

58. A system according to claim 46, said suspect selection unit including:
- an image thresholding unit that generates a set of sliced threshold images; and
- a sphericity testing unit that performs sphericity testing on the same location in each one of the sliced threshold images.

* * * * *